United States Patent
Harks et al.

(10) Patent No.: US 11,628,014 B2
(45) Date of Patent: Apr. 18, 2023

(54) NAVIGATION PLATFORM FOR A MEDICAL DEVICE, PARTICULARLY AN INTRACARDIAC CATHETER

(71) Applicant: KONINKLIJKE PHILIPS N.V., Eindhoven (NL)

(72) Inventors: Godefridus Antonius Harks, Rijen (NL); Frans Venker, San Diego, CA (US); Harm Jan Willem Belt, Weert (NL); Reinardus Gerhardus Aarnink, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 605 days.

(21) Appl. No.: 16/469,716

(22) PCT Filed: Dec. 20, 2017

(86) PCT No.: PCT/EP2017/083950
§ 371 (c)(1),
(2) Date: Jun. 14, 2019

(87) PCT Pub. No.: WO2018/115200
PCT Pub. Date: Jun. 28, 2018

(65) Prior Publication Data
US 2019/0357987 A1    Nov. 28, 2019

Related U.S. Application Data

(60) Provisional application No. 62/436,509, filed on Dec. 20, 2016.

(30) Foreign Application Priority Data

May 17, 2017 (EP) .................................. 17171529

(51) Int. Cl.
*A61B 34/20* (2016.01)
*A61B 34/10* (2016.01)
(Continued)

(52) U.S. Cl.
CPC ............ *A61B 34/20* (2016.02); *A61B 8/4245* (2013.01); *A61B 2034/105* (2016.02);
(Continued)

(58) Field of Classification Search
CPC ..... A61B 34/20; A61B 8/4245; A61B 8/0883; A61B 8/5246; A61B 2034/105;
(Continued)

(56) References Cited

U.S. PATENT DOCUMENTS 6,556,695 B1 * 4/2003 Packer ..................... A61B 8/12
382/128
8,333,705 B2   12/2012 Hauck
(Continued)

FOREIGN PATENT DOCUMENTS

EP    1312309 A1    5/2003
EP    2204121 A1    7/2010
(Continued)

OTHER PUBLICATIONS

Lu, H. et al., "A New Sensor Technology for 2D Ultrasound-Guided Needle Tracking", MICCAI, 2014, Part II, LNCS 8674.
International Search Report and Written Opinion, International Application No. PCT/EP2017/083950, dated Mar. 27, 2018.

*Primary Examiner* — Sean D Mattson

(57) ABSTRACT

The invention relates to a system for assisting in navigating a medical device (1) in a region of a patient body, such as a cardiac chamber. The system comprises a unit (5) for providing a three-dimensional model of the region and an ultrasound probe (2) for acquiring image signals of the region of the patient body. At least one an ultrasound sensor
(Continued)

(6) is attached to the medical device (1) for sensing ultrasound signals emitted by the 5 ultrasound probe (2) and a tracking unit (7) determines a relative position of the at last one ultrasound sensor (6) with respect to the live images and/or the ultrasound probe (2) on the basis of the sensed ultrasound signals. Further, a mapping unit (8) maps the determined relative position of the at least one ultrasound sensor (6) onto the model to generate a visualization of region of the patient body.

15 Claims, 4 Drawing Sheets

(51) Int. Cl.
    *A61B 90/00*     (2016.01)
    *A61M 25/01*     (2006.01)
    *A61B 8/00*     (2006.01)

(52) U.S. Cl.
    CPC ........... *A61B 2034/2063* (2016.02); *A61B 2034/2065* (2016.02); *A61B 2090/364* (2016.02); *A61B 2090/367* (2016.02); *A61B 2090/3786* (2016.02); *A61M 25/0108* (2013.01)

(58) Field of Classification Search
    CPC .... A61B 2034/2063; A61B 2034/2065; A61B 2034/2051; A61B 2034/2061; A61B 2090/364; A61B 2090/367; A61B 2090/3786; A61B 2090/3784; A61B 2017/00243; A61B 2017/00699; A61B 2017/00703; A61M 25/0108
See application file for complete search history.

(56) References Cited

U.S. PATENT DOCUMENTS

| | | |
|---|---|---|
| 2006/0122514 A1 | 6/2006 | Byrd et al. |
| 2006/0193504 A1 | 8/2006 | Salgo |
| 2006/0253031 A1* | 11/2006 | Altmann ............... A61B 5/062 600/466 |
| 2006/0270934 A1* | 11/2006 | Savord ............... G01S 7/52068 600/437 |
| 2009/0149740 A1 | 6/2009 | Hoheisel |
| 2012/0259209 A1 | 10/2012 | Harhen |
| 2013/0041252 A1* | 2/2013 | Vignon ............... A61B 8/5207 600/424 |
| 2013/0245433 A1* | 9/2013 | Deladi ............... A61B 8/0883 600/424 |
| 2014/0343416 A1 | 11/2014 | Panescu et al. |
| 2016/0113632 A1* | 4/2016 | Ribes ............... A61B 8/5269 600/440 |
| 2016/0249885 A1* | 9/2016 | Schneider ........... A61B 8/0883 382/131 |
| 2016/0331469 A1* | 11/2016 | Hall ..................... A61B 8/4218 |

FOREIGN PATENT DOCUMENTS

| | | | |
|---|---|---|---|
| JP | 2006305361 A | 11/2006 | |
| WO | 2008103383 A1 | 8/2008 | |
| WO | 2011138698 A1 | 11/2011 | |
| WO | 2012091763 A1 | 7/2012 | |
| WO | 2015092667 A1 | 6/2015 | |
| WO | WO-2015092667 A1 * | 6/2015 | ............ A61B 8/466 |
| WO | 2016009350 A1 | 1/2016 | |
| WO | WO-2016009350 A1 * | 1/2016 | ............ A61B 34/20 |
| WO | 2016108110 A1 | 7/2016 | |

\* cited by examiner

NAVIGATION PLATFORM FOR A MEDICAL DEVICE, PARTICULARLY AN INTRACARDIAC CATHETER

CROSS-REFERENCE TO PRIOR APPLICATIONS

This application is the U.S. National Phase application under 35 U.S.C. § 371 of International Application No. PCT/EP2017/083950, filed on 20 Dec. 2017, which claims the benefit of U.S. Provisional Patent Application No. 62/436509, filed on 20 Dec. 2016 and European Patent Application No. 17171529.5, filed on 17 May 2017. These applications are hereby incorporated by reference herein.

FIELD OF THE INVENTION

The invention relates to a system and a method for assisting a user in navigating a medical device in a region of a patient body. Moreover, the invention relates to a computer program for carrying out the method. The region of the patient body may particularly be a cardiac chamber and the medical device may particularly be an intracardiac catheter or another intracardiac device.

BACKGROUND OF THE INVENTION

Interventional cardiology procedures, including electrophysiology (EP) and structural heart disease (SHD) procedures rely on the use of fluoroscopy that allows real-time visualization of the anatomy and of radiopaque devices used in these procedures. The major disadvantage of fluoroscopy is however the exposure of the patient and staff to radiation doses. Therefore, there is a trend and desire to minimize the use of fluoroscopy during these procedures. Another disadvantage of fluoroscopy is the inability to visualize soft-tissue structures.

Ultrasound (US) imaging is also often used in these procedures, including intracardiac echocardiography (ICE), transesophageal echocardiography (TEE) and transthoracic echocardiography (TTE). US imaging has the advantage that it allows for the visualization of soft-tissue structures and blood flow without harmful scatter radiation. Devices such as catheters and needles can be visualized using ultrasound. However, it is often difficult to identify the tip of such a device, in particular when using two-dimensional ultrasound, because the device can be out of the imaged plane and because shadowing and reverberations complicate the identification of the tip.

Navigation platforms for navigating medical devices in cardiology procedures therefore may use additional hardware for tracking the medical device in accordance with a certain tracking modality such as electromagnetic (EM) tracking, impedance tracking, optical shape sensing or satellite-based tracking. However, these tracking modalities give rise to inaccuracies with respect to the localization of medical device relative to the anatomy as e.g. shown in the US images.

Likewise, if the tracked devices are used to reconstruct the anatomy of the heart or another body region as in electro-anatomical mapping, for example, the generated representation of the anatomy may be inaccurate due to inaccuracies in the tracking of the devices. In EM tracking, such inaccuracies may particularly be due to metal in the environment which can cause disturbances. For impedance tracking, patches on the patient surface are used as reference but inhomogeneities in impedances for various tissues (e.g. cardiac and lung) and changes in volume load during the procedure can create inaccuracies. For optical shape sensing, a fixture at the patient table is used as a reference and the position error of this fixture propagates over the length of the optical fiber. For satellite-based tracking, such as tracking using the Global Positioning System (GPS), also the localization is independent of anatomy.

SUMMARY OF THE INVENTION

It is an object of the present invention to provide a navigation platform that mitigates the aforementioned problems and allows for a more accurate localization of a medical device with respect to the anatomy as shown in US images thereof.

In accordance with a first aspect, the invention provides a system for assisting a user in navigating a medical device in a region of a patient body. The system comprises: (i) a 3D model providing unit configured to provide a three-dimensional model of the region of the patient body, (ii) an ultrasound probe for acquiring image signals of the region of the patient body and an ultrasound unit configured to provide live images of the region of the patient body on the basis of the image signals, (iii) at least one ultrasound sensor attached to the medical device for sensing ultrasound signals emitted by the ultrasound probe, (iv) a tracking unit configured to determine a relative position of the at last one ultrasound sensor with respect to the live images and/or the ultrasound probe on the basis of the sensed ultrasound signals, and (v) a mapping unit configured to map the determined relative position of the at least one ultrasound sensor onto the model to generate a visualization of the region of the patient body on the basis of the model and on the basis of the result of the mapping.

Since the position of the medical device is tracked by determining the relative position of the at least one ultrasound sensor with respect to the ultrasound probe on the basis of the ultrasound signals emitted by the ultrasound probe and sensed by the ultrasound sensor, it is possible to accurately track the medical device in relation to the anatomy of the region of the patient body as imaged by means of the ultrasound probe. Further, the position of the ultrasound sensor and, thus, of the medical device can be displayed in relation to a model of the relevant region of the patient body. This is done on the basis of the mapping of the position onto the model, which particularly corresponds to a transformation of the position into a reference frame in which the model is defined.

In one embodiment, the mapping unit is configured to generate a visualization of the model in which the position of the at least one ultrasound sensor is marked. In a related embodiment, the mapping unit is further configured to map the live images onto the model and to overlay the model with the live images in the visualizations on the basis of the result of this mapping. In these embodiments, it is possible to visualize the position and/or orientation of the medical device with respect to the anatomy as represented by the model and, optionally, also with respect to the live images. On the basis of these visualizations, the medical device can be accurately steered within the region of the patient body.

In a further related embodiment, the mapping unit is configured to map the live images onto the model on the basis of an image comparison of the live images and the model. The image comparison may particularly be carried out on the basis of fiducial features in the live images and corresponding features of the model. On the basis of the image comparison, the live images can be mapped onto the model relatively quickly and easily.

In a further embodiment, the mapping unit is configured to map the live images onto the model on the basis of a relative position and orientation of the ultrasound probe with respect to a reference frame associated with the model. It is an advantage of this embodiment that the mapping on the basis of the position and orientation information allows for a very accurate matching of the live images and the model.

In the mapping procedure, the position information may be taken into consideration in addition to the comparison of the live images and the model in order to improve the accuracy of the mapping. Likewise, it is possible to carry out the mapping on the basis of the comparison or on the basis of the position and orientation information alone.

In a one embodiment, the 3D model providing unit is configured to create the model using ultrasound images acquired using the ultrasound probe during an initialization phase in which a further ultrasound sensor is positioned at a reference position and the reference frame is defined on the basis of a relative position and orientation of the ultrasound probe with respect to the further ultrasound sensor determined on the basis of the ultrasound signals sensed by the further ultrasound sensor. A related embodiment includes that the further ultrasound sensor is positioned at the reference position during the acquisition of the live images and that the mapping unit is configured to determine the relative position and orientation of the ultrasound probe with respect to the reference frame on the basis of the relative position and/or orientation of the further ultrasound sensor with respect to the ultrasound probe.

In these embodiments, the further ultrasound sensor may be attached to a further medical device. This medical device may be held a fixed position during the initialization phase and during the procedure, in which the position of the aforementioned at least one ultrasound sensor is tracked, so that the position of the further ultrasound sensor mounted on the device can be used in the aforementioned way as a position reference. In exemplary implementations of these embodiments, the further medical device may specifically be used in order to provide a position reference. In alternative implementations, the further medical device may have another function during the procedure. An example of such a further medical device is a diagnostic electrophysiology (EP) catheter which may be used for sensing electrical signals or for applying electrical signals to tissue for stimulation.

Likewise, it is possible to track the ultrasound probe independently of the position of a further ultrasound sensor. In this respect, one embodiment includes that the system further comprises a tracking arrangement for determining the position and orientation of the ultrasound probe with respect to the reference frame, the tracking arrangement using at least one tracking technique from the group comprising electromagnetic tracking, impedance tracking, optical shape sensing and satellite-based tracking.

The region of the patient body may undergo a periodic motion having different motion phases. In this respect, one embodiment includes that the model is a dynamic model comprising a deforming sub-model for each of the motion phases and that the mapping unit is configured to determine a current motion phase and to map the relative position of the at least one ultrasound sensor on the deforming sub-model for current motion phase. This allows for generating visualizations for different phases of the periodic motion of the region of the patient body. The periodic motion of the region of the patient body may be due to cardiac motion and/or due to respiratory motion. The current motion phases may be identified on the basis of the live ultrasound images. Likewise, other techniques may be applied to identify the motion phases.

In a further embodiment, the medical device is configured to carry out electrical measurements to generate an electro-anatomical map of the region of the patient body and wherein the mapping unit is configured to overlay the electro-anatomical map over the model on the basis of the relative position of the at least one ultrasound sensor with respect to the ultrasound probe during the measurements. The electro-anatomical map may particularly comprise an activation map and/or a voltage map of the region of the patient body which may include a region of the patient's heart. By generating the electro-anatomical map on the basis of the position information determined using the at least one ultrasound sensor, an accurate map of the relevant region of the patient body can be determined.

In a further embodiment, the mapping unit is configured to generate a visualization of the model corresponding to a view as seen by a virtual eye based on the position of the at least one ultrasound sensor. The virtual eye may particularly be located at the position of the at least one ultrasound sensor. In such a way the anatomy of the relevant region of the patient body can be viewed from the point of view the ultrasound sensor which may particularly be attached to the tip of the medical device. In further implementations of these embodiments, the virtual eye may be positioned at the location of a certain anatomical landmark presented in the three-dimensional model.

The view as seen by the virtual eye particularly comprises parts of the model which are included in a field of view of the virtual eye. The field of view of the virtual eye may particularly be directed along the longitudinal direction of the distal end section of the medical device in this case and cover a region in front of the medical device.

In a related embodiment, the mapping unit is configured to map the live images onto the view and to overlay the view with the live image in the visualization on the basis of the result of the mapping. In a further related embodiment, the mapping unit is configured to generate the visualization on the basis of a mapping of the live image and/or the position and orientation of the ultrasound probe to the model and on the basis of the relative position and orientation of the at least one ultrasound sensor with respect to the ultrasound probe.

With respect to the determination of the relative position of the at least one ultrasound sensor with respect to the ultrasound probe, one embodiment includes that the ultrasound probe is configured to emit ultrasound signals into different directions and that the tracking unit is configured to determine the position of the at least one ultrasound sensor based on a reception level of the ultrasound signals in ultrasound sensor. In a further embodiment, the tracking unit is configured to determine the position of the at least one ultrasound sensor on the basis of a time difference between the emission of the ultrasound signals by the ultrasound probe and their sensing by the ultrasound sensor.

In accordance with a further aspect, the invention provides a method for assisting a user in navigating a medical device in a region of a patient body. The method comprises: (i) providing a three-dimensional model of the region of the patient body, (ii) obtaining live images of the region the patient body on the basis of image signals acquired using an ultrasound probe, (iii) determining a relative position of at least one an ultrasound sensor attached to the medical device with respect to the ultrasound probe, the ultrasound sensor sensing ultrasound signal emitted by the ultrasound probe, (iv) mapping the determined relative position of the at least one ultrasound sensor onto the model to generate a visualization of the region of the patient body on the basis of the model and on the basis of the result of the mapping.

In accordance with a further aspect, the invention provides a computer program comprising program code for instructing a computer device to perform the method, when the computer program is executed on the computer device.

It shall be understood that the system of claim 1 and the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
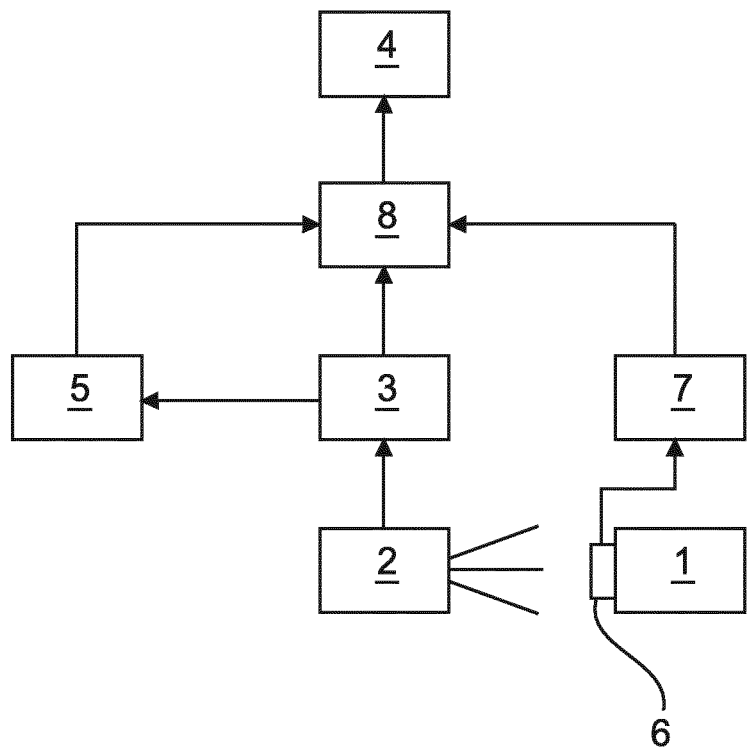
FIG. 1 schematically and exemplarily shows components of a system for navigating a medical device in a region of a patient body, FIG. 2 schematically and exemplarily shows a three-dimensional model of a left atrium of a heart, FIG. 3*a* schematically and exemplarily shows a two-dimensional slice corresponding to a field of view of an US probe of the system, which is mapped onto the model, FIG. 3*b* schematically and exemplarily shows a three-dimensional cone corresponding to a field of view of an US probe of the system, which is mapped onto the model, FIG. 4 schematically and exemplarily shows a visualization in which a live US-image and a position of the medical device is overlaid over the model, FIG. 5 schematically and exemplarily shows on overlay of a current position and preceding positions of an US sensor attached to the medical device over the model, FIG. 6 schematically and exemplarily shows steps of a procedure for generating visualizations in which a position of a medical device is shown using a model.

FIG. 1 schematically and exemplarily shows components of a system for navigating a medical device 1 in a region of a patient body, which may particularly correspond to a cardiac chamber. The system allows for visualizing the relevant region of the patient body and a position and/or orientation of one or more medical device(s) 1 used in the region of the patient body to a physician performing an interventional procedure using the medical device. On the basis of the generated visualizations, the physician can steer the medical device 1 during the interventional procedure.

The medical device 1 may be a catheter, particularly an ablation catheter, a needle or a guidewire, for example. The system may particularly be used for carrying out structural heart disease procedures including valve replacement/repair (e.g. Transcatheter Aortic Valve Replacement (TAVR), mitraclip, pulmonic valve, tricuspid valve etc.) and occlusions (e.g. ASD/PFO closure, VSD closure, left atrial appendage closure, etc.). Moreover, the system may be used in electrophysiology (EP) studies with ablation, including catheter ablation procedure for treatment of arrhythmias including atrial fibrillation (AF).

The system comprises a miniaturized US probe 2 which includes an US transducer for emitting US signals and for sensing echoes of the US signals in order to generate US images with respect to a certain field of view. During the interventional procedure, the US probe 2 is inserted into the patient body to acquire live US images of the relevant body region essentially in real-time. In order to insert the US probe 2 into the patient body, it may be attached to a catheter or a similar elongated device.

The US probe 2 is configured to acquire three- or two-dimensional US images. In order to the generate the US images, the US signals sensed by means of the US probe 2 are processed in a US unit 3 which is located external to the patient body and connected to the US probe 2 and which is configured to generate the US images on the basis of US signals in a manner known to the person skilled in the art as such.

In case the relevant region of the patient body includes a cardiac chamber, the US probe 2 is preferably inserted into the heart to image the relevant cardiac chamber in accordance with an ICE technique. However, the US probe 2 may likewise be configured and utilized in accordance with another echocardiography technique known to a person skilled in the art, such as echocardiographic imaging from the esophagus as in TEE or echocardiographic imaging from a position external to the patient body as in TTE.

Moreover, the system comprises a tracking arrangement for determining the position and/or orientation of the medical device 1 relative to the US probe 2. This tracking arrangement will be described in more detail further below. On the basis of the relative position and/or orientation of the medical device 1 with respect to the US probe 2, the system generates the visualization of the position and/or orientation of the medical device 1 in the relevant region of the patient body.

In the system, the visualization of the relevant region of the patient body and of the position and/or orientation of the medical device 1 positioned therein is based on a three-dimensional model of the relevant region of the patient body. More specifically, the system may generate visualizations in which the live US images and indications of the position and/or orientation of the medical device are overlaid over the model. In addition or as an alternative, the system may generate visualizations which include a part of the model included in the field of view of a virtual eye at the tip of the medical device 1. This part of the model may further be overlaid by the live US images in the visualizations.

For displaying the visualizations of the volume of interest and of the position and/or orientation of the medical device 1, the system further comprises a display unit 4. The display unit 4 may comprise a monitor screen. Likewise, the display unit 4 may be configured in another way and may comprise virtual reality glasses, for example.

Figure 2:
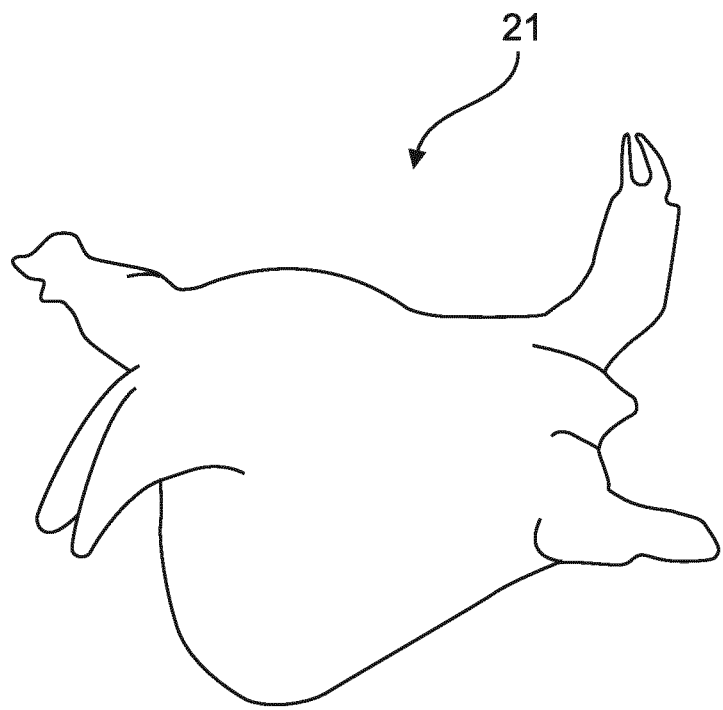

The three-dimensional model of the relevant region of the patient is preferably created prior to the actual interventional procedure during which the live US images are acquired and stored in a 3D model providing unit 5 for use during the actual interventional procedure. By way of example, a corresponding model 21 of the left atrium of the heart is schematically illustrated in FIG. 2.

In one implementation, the model is created on the basis of a series of US images acquired using the US probe 2 during an initialization phase preceding the actual interventional procedure. During this initialization phase, the US probe 2 may be moved to image relevant region of the patient body essentially completely in a series of US images. Then, the 3D model providing unit 5 may create the model by combining the US images, particularly by stitching the US images. For this purpose, any stitching technique known the person skilled in the art may be applied.

If the relevant region of the patient body comprises the left atrium of the heart, as it is the case in ablation of atrial fibrillation (AF), for example, it may be imaged from the right atrium through the interatrial septum. For this purpose, the US probe 2 is placed at an appropriate position in the right atrium and is operated to acquire a series of US images of the left atrium under different viewing angles so that the left atrium is imaged essentially completely. On the basis of these images, a model of the left atrium may then be created in the 3D model providing unit 5 by stitching the acquired US images. As an alternative, the US probe 2 may be positioned within the left atrium for acquiring the series of images of the left atrium under different viewing angles. For this purpose, a transseptal puncture can be made in order to cross the interatrial septum with the US probe 2. In this procedure, a sufficiently small US probe 2 may be used which allows for a safe transseptal crossing. In order to acquire images of the complete left atrium, the US probe 2 may be moved in a suitable combination of translations, deflections and rotations.

During the acquisition of the series of images used for creating the model, the positions and orientation of the US probe 2 may optionally be tracked with respect to a certain reference frame in order to determine the position and orientation of the model in this reference frame. As will be explained further below, the position and orientation may be used in the process of mapping the live US images onto the model. For tracking the position and orientation of the US probe 2, any suitable tracking technique known to a person skilled in the art may be used. Examples of such tracking techniques include a tracking on the basis of images of the relevant region of the patient body acquired using a suitable imaging modality, such as fluoroscopy, or EM tracking, impedance tracking, optical shape sensing and satellite-based tracking.

In accordance with a further approach, the position and orientation of the US probe 2 may be tracked relative to the position and orientation of a further medical device in a manner further described below, when the further medical device, which is also referred to a reference device herein below, is positioned at a fixed reference location during the initialization phase and during the actual interventional procedure. In this case, the reference device defines the reference frame for the tracking of the US probe 2.

In further implementations, the model of the relevant body region of a particular patient may be selected from a plurality of pre-generated models for the same body region, which may be generated on the basis of data collected for other patients and stored in a corresponding library. These models may likewise be created on the basis of US image data. Alternatively, these models may be created on the basis of imaging data of another imaging modality, such as computed tomography (CT imaging) or magnetic resonance (MR) imaging. From the pre-generated models, one model may be selected which best matches with the anatomy of the patient.

The selection of the best matching model may again be carried out on the basis of US images acquired during an initialization phase. In particular, the model may be selected, which has the largest similarity to the US images in accordance with the suitable similarity measure. The similarities between an US image and the model may be determined on the basis of a segmented version of the US image, which may be computed using a suitable procedure known the person skilled in the art. The similarity measure may be computed on the basis of the number of overlapping points between the segmented US image and the model for the best overlap between the segmented US image and the model. On the basis of the determined position and orientation of the US probe 2 at the time of the acquisition of the US images, the position and orientation of the selected model in a reference frame may again be determined as described above.

In further alternatives, the three-dimensional model may be created on the basis of images of the relevant body region which are not acquired using the US probe 2 but using another imaging modality. For instance, in case the US probe 2 is an ICE probe, the images may be acquired using another US imaging modality, such as TEE or TTE Likewise, another imaging modality may be used to acquire one or more image(s) for creating the model, such as, for example computed tomography (CT) imaging, magnetic resonance (MR) imaging or 3D rotational angiography (3DATG). Also in these implementations, the position and orientation of the model in a reference frame may be determined, e.g. by tracking the utilized US probe or on the basis of the known image frame of the CT or MR image.

Further, when the relevant body region moves periodically during the interventional procedure, as it is particularly the case if the relevant body region includes a cardiac chamber, the three-dimensional model of the relevant body region may represent the body region in one particularly phase of its periodic motion. In this implementation, visualizations may only be generated for the relevant motion phase. This particularly means that only live US images and position and/or orientation information acquired during the relevant motion phase are used in the system. These data may be selected on the basis of a gating signal, which indicates the start and end of the relevant motion phase in each cycle of the periodic motion.

In case the relevant body region includes a cardiac chamber, the relevant motion phase may correspond to the systole or the diastole. The gating signal may be derived from an electrocardiography (ECG) signal for, example. As an alternative, any other signal varying in synchronization with the periodic motion of the heart may be used. So, the gating signal may be derived from position and/or orientation information of the US probe 2 and/or the tracked medical device 1. Likewise, the gating signal may be derived from the live US images acquired by means of the US probe 2. In this embodiment, a statistical property of the live US images varying in synchronization with the period motion of the heart, such as the mean pixel value (in case of two-dimensional images) or voxel value (in case of three-dimensional images) or the variance of all pixel or voxel values, may be evaluated, and the gating signal may be derived from the variations of this property.

Moreover, a gating mechanism may be applied with respect to other motions of the heart, such as respiratory motion. In this case, the model of the heart may be created for a particular phase of the respiratory motion of the heart, and only live US images and position and/or orientation information acquired during this phase are used in the system for generating a visualization. For determining the occurrence of the relevant phase of the respiratory motion, the system may further comprise a sensor for determining the respiratory motion, such as, for example, a sensor for determining the ventilation air flow and/or a sensor for determining the movement of the patient's chest or abdominal wall during breathing. On the basis of the signals of this sensor, the data including the live US images and the position and/or orientation data are unlocked (for the relevant phase of the respiratory motion) or locked (during other phases of the respiratory motion) for the creation of visualizations.

As an alternative to a static model and the aforementioned gating, a dynamic model may be used. This model may include deforming sub-models for each relevant phase of the periodic motion of the relevant body region, where of each deforming sub-model models the changing form of the relevant body region. These sub-models may be defined on the basis of vector fields describing the displacement of image portions of the model with time during the motion phases. In each of the motion phases, the system uses the associated sub-model for generating the visualizations on the basis of live US images and position and/or orientation information for the tracked medical device 1 acquired during this motion phase. Corresponding sub-models may be created for different phases of the cardiac motion and/or for the respiratory motion of the relevant body region.

For identifying the relevant motion phases in this alternative, suitable trigger signals are used, which may be derived in a similar manner as the aforementioned gating signals. In case the relevant region of the patient body includes a cardiac chamber, the trigger signals may particularly again be derived from an ECG signal or from another signal varying in synchronization with the heart motion. Optionally, the dynamic model may also be generated for different phases of the respiratory motion of the heart and the corresponding phases may be identified using a sensor for determining the respiratory motion.

In the way described above, models of various regions of interest may be created. One such region may be the left atrium as described above. In a similar manner, models can particularly be created for other heart chambers, such as the right atrium, left and right ventricle, or for vessels such as the aorta, pulmonary artery, pulmonary veins, inferior vena cava, superior vena cava, coronary arteries, coronary veins, or for a valve anatomy, such as the aortic valve, mitral valve, tricuspid valve, pulmonary valve, or the esophagus.

The tracking arrangement for determining the position and/or orientation of the medical device 1 relative to the US probe 2 includes at least one US sensor 6 attached to the medical device 1, particularly to its tip. The US sensor 6 is configured to sense US signals incident onto the US sensor 6. For this purpose, the US sensor 6 may comprise a foil of US sensitive material. Likewise, the US sensor 6 may comprise an US transducer, such as for example, a lead zirconium titanate (PZT) transducer, a single crystal transducer (SXL), a capacitive micro-machined ultrasonic transducer (CMUT) or a piezoelectric micro-machined ultrasonic transducer (PMUT), where only the ability to sense US signals is used here. During operation in the present system, the US sensor 6 senses US signals emitted by the US probe 2.

The US sensor 6 is connected to a tracking unit 7 which determines the relative position of the US sensor 6 with respect to the US probe 2 on the basis of the sensed US signals and, thus, determines the relative position of the tip of the medical device 1 with respect to the US probe 2. In order to determine the orientation of the medical device 1, at least one further US sensor 6 is attached to the medical device 1 and the tracking unit 6 also determines the relative position of the further US sensor 6 with respect to the US probe 2 on the basis of the US signals sensed by the further US sensor 6. On the basis of the relative positions of the US sensors 6, the tracking unit then determines the orientation of the medical device 1.

In order to ascertain the position of one US sensor 6, the tracking unit 7 evaluates the US signals sensed by the US sensor 6 while the US probe 2 images the volume of interest by emitting US beam pulses under different azimuth angles and, in case of a 3D US probe 2, also under different elevation angles. In order to determine the angular position of the US sensor 6 with respect to the US probe, the tracking unit 7 compares the responses to the emitted US beams sensed by the US sensor 6 and determines the azimuth angle and, in case of a 3D US probe 2, also the elevation angle under which the beam(s) resulting in the maximum response(s) have been emitted. The determined angle(s) define(s) the relative angular position of the US sensor 6 with respect to the US probe 2. The distance between the US sensor 6 and the US probe 2 is determined on the basis of the time delays between the times of the transmission of the beams producing the maximum responses and the times of the sensing of the beams by the US sensor 6, i.e. on the basis of the time of flight of the beams.

Exemplary implementations of this tracking technique are also described in WO 2011/138698A1 and in the publication "A New Sensor Technology for 2D Ultrasound-Guided Needle Tracking", Huanxiang Lu et al, MICCAI 2014, Part II, LNCS 8674, pp. 389-396, 2014. In the present system, the tracking technique may be implemented in a similar manner.

As said above, in one embodiment the system generates visualizations in which the live US images and indications of the position and/or orientation of the medical device 1 are overlaid over the model of the relevant region of the patient body. These visualizations are displayed at the display unit 4 during an interventional procedure in order to assist the physician in steering the medical device 1 during the interventional procedure.

Figure 3A:
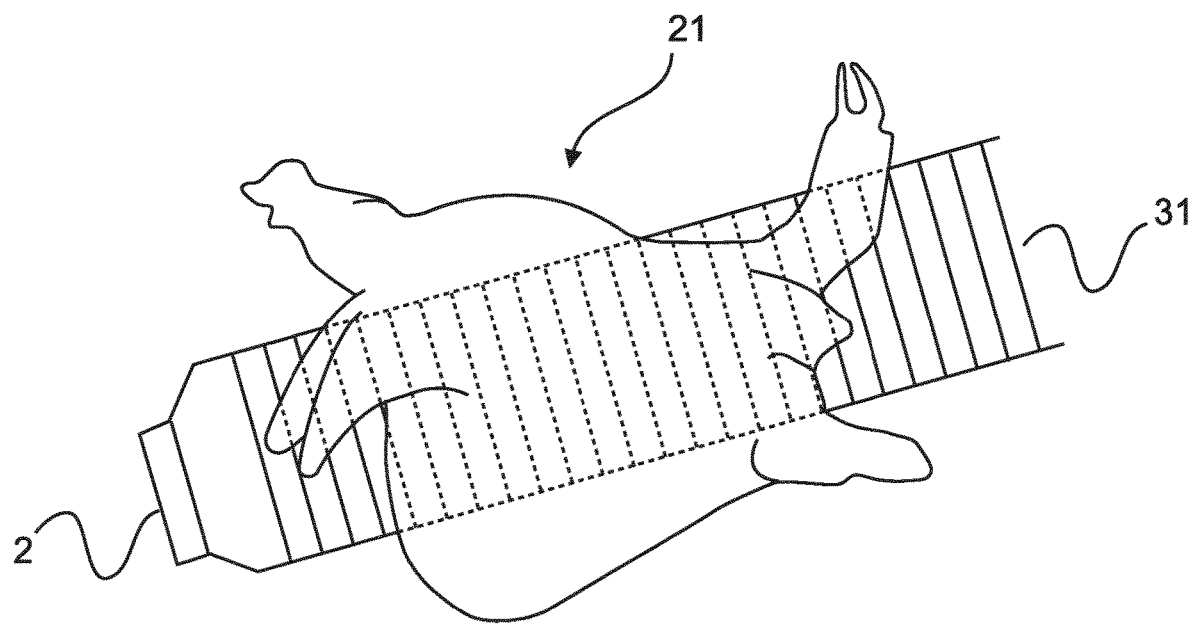
Figure 3B:
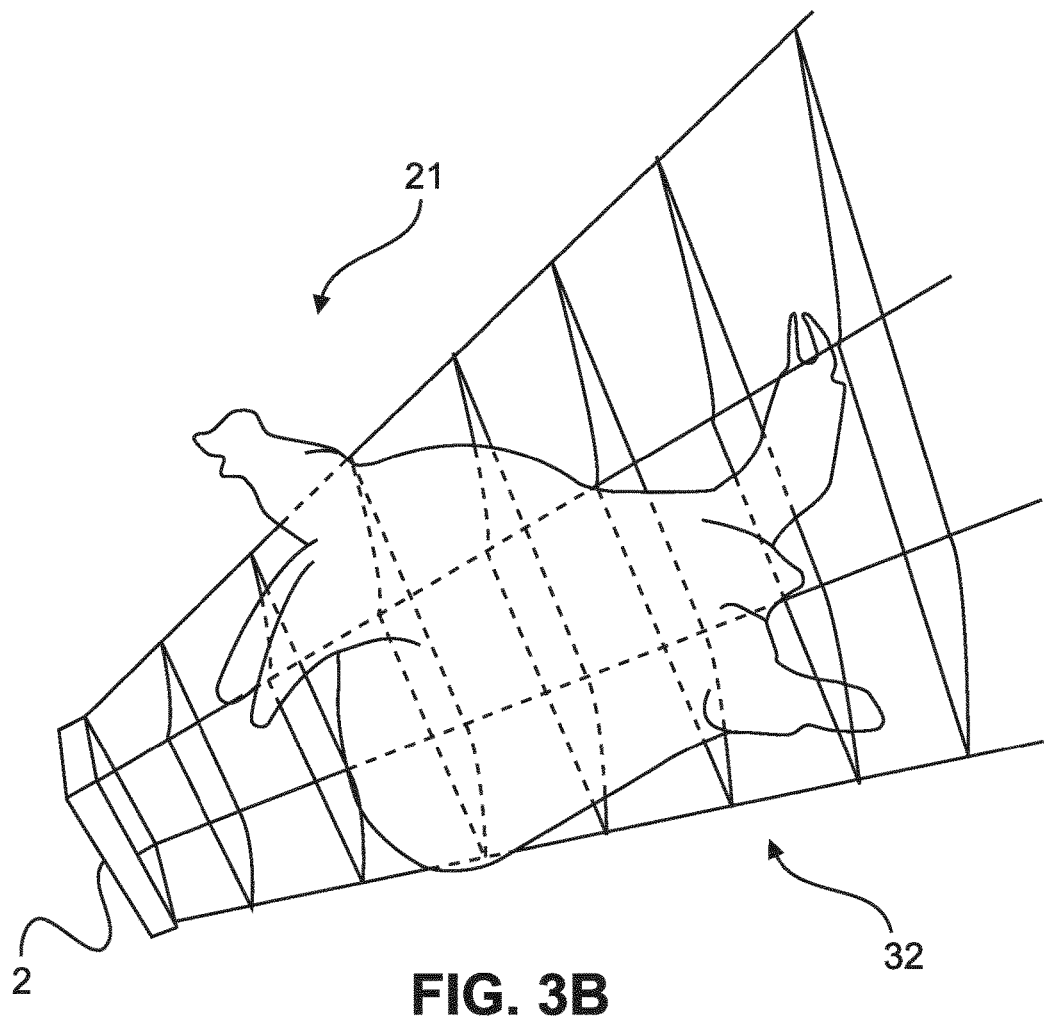

In order to generate these visualizations, a mapping unit 8 of the system maps the live US images acquired using the imaging probe 2 onto the model of the relevant region of the patient body provided by the 3D model providing unit 5. Thus, the mapping unit 8 determines the part of the model which is included in the live images. In FIG. 3a, this mapping is schematically and exemplarily illustrated for a two-dimensional slice 31 corresponding to a field of view of an US probe 2 for acquiring two-dimensional images, which is mapped onto the model 21 of the left atrium shown in FIG. 2. FIG. 3b schematically and exemplarily illustrated the mapping for a three-dimensional cone 32 corresponding to a field of view of an US probe 2 for acquiring three-dimensional images, which is mapped onto the model 21 of the left atrium shown in FIG. 2.

In one implementation, the mapping of a live US image onto the model is performed on the basis of the comparison between the live US image and the model. In particular, an image registration between the live US image and the model may be carried out which involves the determination of a rigid transformation for transforming the US image such that it matches a portion of the model. The rigid transformation comprises a rotation and/or a translation.

In one embodiment of the registration procedure, the mapping unit 8 may identify fiducial image points in the live US image and map these image points to corresponding points of the model in order to determine the transformation. The mapping of fiducial points can be carried out using known computer vision techniques, such as, for example, scale-invariant feature transform (SIFT). Alternatively, a registration method may be applied which determines the rigid transformation such that the transformed live US image has the largest similarity to the model. Such a registration procedure may be performed on the basis of a segmented version of the live US image, which may be determined using a suitable segmentation procedure known the person skilled in the art. The similarity between the (transformed) US image and the model may again be determined on the basis of a suitable similarity measure, e.g. as explained above.

In case the model is a dynamic model, the mapping of the live US image onto the model may also be made by matching estimated motion vectors describing the displacement of image portions in the live image pertaining to one motion phase relative to the positions of the image portions in a live image of the preceding motion phase with the motion vectors describing the displacement of image portions of the dynamic model.

The mapping of the live US images onto the model may be performed on the basis of the aforementioned image registration procedure alone. In this case, the determined transformation may also be evaluated to determine the relative position of the US probe 2 with respect to the model, i.e. in the reference frame in which the model is defined.

In addition or as an alternative, the mapping of a live US image onto the model may be performed on the basis of information about the position and orientation of the US probe 2 in case the position and orientation of the model has been determined with respect to a reference frame as explained above. Using this position and orientation information, the mapping unit 8 may determine a rigid transformation for transforming the live US image into the reference frame in which the model is defined and maps the live US image onto the model by applying this transformation. The transformation may be determined on the basis of the information about position and orientation of the US probe 2 alone or it may be determined based on this information and additionally based on an image registration between the live US image and the model as explained above.

In order to carry out the mapping in this embodiment, the position and orientation of the US probe 2 at the time of the acquisition of the live image within the reference frame is determined. On this basis, the mapping unit 8 further determines the relative position and orientation of the field of view of the US probe 2 with respect to the model and uses this information for determining which part of the model is imaged by the US probe 2 in the live US image.

The determination of the position and orientation of the US probe 2 with respect to the reference frame may be made using any of the tracking techniques already referred to above in connection with the description of the creation of the model. Thus, it may be determined on the basis of images of the relevant body region acquired using a suitable imaging modality, such as fluoroscopy, or on the basis of EM tracking, impedance tracking, optical shape sensing or satellite-based tracking.

Further, as described above, the position and orientation of the US probe 2 may likewise be tracked with respect to the reference device when the reference device is held at the same fixed position during the initialization phase in which the model is created and during the actual interventional procedure. In this implementation, the position and orientation of the reference device defines the reference frame of the model.

For determining the relative position and orientation of the US probe 2 with respect to the reference device during the initialization phase (for creating the model) and during the interventional procedure (for generating visualizations of the basis of the model), the reference device may be equipped with US sensors and on the basis of the US signals sensed by the US sensors, the relative position and orientation of the US probe 2 and the reference device is determined as explained above in connection with the medical device 1. On the basis of this information, the position and orientation of the US probe 2 relative to the model is determined.

The reference device may be specifically provided in order to establish a reference position and orientation for the tracking of the US probe 2. Alternatively, the reference device may be a medical device which has another function during the interventional procedure but is substantially not moved during the procedure, such as, for example, a diagnostic EP catheter for sensor electrical signals or applying electrical signals to tissue for stimulation.

Figure 4:
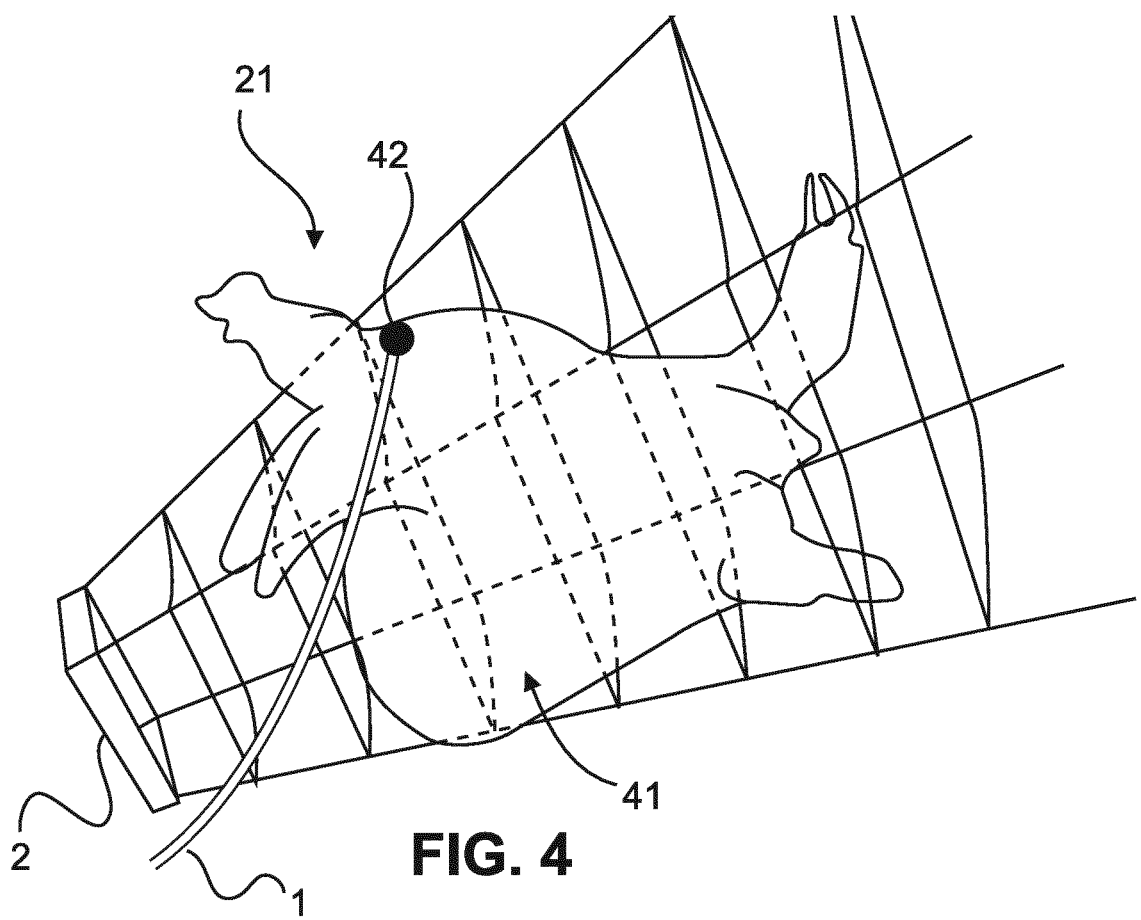

Upon having mapped the live US image onto the model, the mapping unit 8 may create a visualization in which the live US image is overlaid over the model in accordance with the result of the mapping. Further, the mapping unit 8 marks the position(s) of the US sensor(s) 6 attached to the medical device 1 in the visualization, i.e. in the live US image and the model as included in the visualization. The marking may be made by placing corresponding dots or other symbols in the visualization. The visualization is then displayed at the display unit 4 of the system. A corresponding visualization is schematically and exemplarily illustrated in FIG. 4 for a three-dimensional US image 41. In the example illustrated in FIG. 4, the medical device 1 is shown in the US image and the position of an US sensor 6 attached to the tip of the medical device 1 is marked with a dot 42.

In order to mark the position(s) of the US sensor(s) 6 in the visualization, the mapping unit 8 determines the relative position(s) of the US sensor(s) 6 attached to the medical device 1 with respect to live US image and/or the model.

This may be done on the basis of the relative position(s) of the US sensor(s) 6 with respect to the US probe 2 as determined in the tracking unit 7 and on the basis of the relative position of the US probe 2 or the live US image acquired using the US probe 2 with respect to the model. These data allow for determining the relative position(s) of the US sensor(s) 6 with respect to the model so that the mapping unit 8 can place the marks in the visualization accordingly.

Likewise, the mapping unit 8 may directly determine the position(s) of the US sensor(s) 6 in the model. This is particularly possible if the position and orientation of the medical device 1 defines the reference frame of the model as describe above.

In one implementation, the mapping unit 8 generates the visualizations in such a way that each of the visualizations shows the current position(s) of the US sensor(s) attached to the medical device 1, i.e. the position(s) at the time of the acquisition of the live US image included in the visualization. Thus, a physician viewing the visualization at the display unit can easily determine the current position and/or orientation of the medical device 1 during the interventional procedure.

Figure 5:
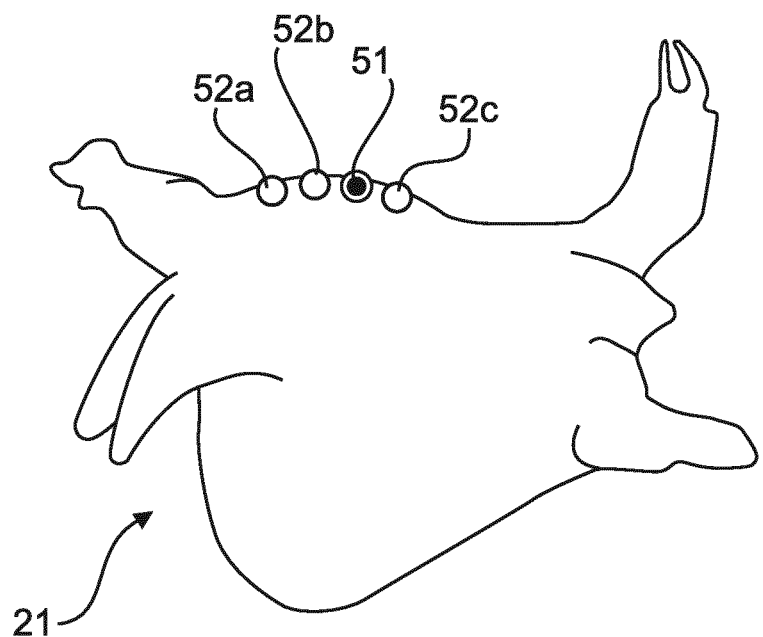

In a further implementation, the mapping unit 8 may generate the visualizations in such a way that previous positions of the one or more of the US sensor(s) 6 attached to the medical device 1 are marked in addition to the current position(s). By way of example, a corresponding visualization is illustrated in FIG. 5. In this visualization, the current position of a US sensor 6 attached to a medical device 1 is indicated by means of a mark 51 in the model 21 of the left atrium and previous positions of the US sensor are indicated by means of marks 52*a-c*.

In particular, the visualizations may be generated such that previous positions of the US sensor 6 attached to the device's tip are additionally marked in the visualizations. This is particularly useful if the medical device 1 is an ablation catheter. In this case, the previous positions may correspond to previous ablation points. These points may be identified manually or automatically during the ablation procedure and stored in the mapping unit 8 in response to their identification so that they can be marked in subsequently generated visualizations. In addition, also ablation parameters such as power and duration, which were used for ablation at the ablation points, or lesion parameters may be stored in the mapping unit 8 and displayed in connection with the marks identifying the ablations points in the visualizations.

In addition or as an alternative to the previous positions of the US sensor 6, the system may mark positions of a planned (future) trajectory of the medical device 1 in the presented visualization in order to assist the physician viewing the visualizations in following the planned trajectory.

In a further embodiment, the mapping unit 8 generates visualizations for displaying at the display unit 4, which comprise a part of the model included in the view of a virtual eye at the location of the US sensor 6 attached to the tip of the medical device 1. The field of view of the virtual eye may particularly be directed along the longitudinal direction of the distal end section of the medical device 1 and cover a region in front of the medical device 1. The visualization may be generated from the three-dimensional model and optionally also from the live US images.

In this embodiment, the mapping unit 8 maps the position and orientation of the medical device 1 on the model. This mapping is performed on the basis of a mapping of plural US sensors 6 attached to the medical device 1 on the model. The latter mapping is carried out directly or on the basis of the mapping of the position and orientation of the US probe 2 onto the model and on the basis of the relative positions of the US sensors 6 with respect to the US probe 2 as already described above. On the basis of the mapping of the position and orientation of the medical device 1 onto the model, the mapping unit 8 then determines the parts of the model which are included in the field of view of the virtual eye and generates the visualization such that it includes these parts in a view which corresponds to the view as seen by the virtual eye.

In addition, the mapping unit 8 may map the live US images acquired by means of the US probe 2 onto the determined view of the model on the basis of a transformation of the US image. For this purpose, the mapping unit 8 may determine a rigid transformation for transforming the image space corresponding to the live US image to a new image space corresponding to the field of view of the virtual eye on the basis of the relative position and orientation of the medical device 1 with respect to the US probe 2. This transformation is then applied to the live US image. Thereupon, the mapping unit 8 generate a visualization in which the transformed live US image is overlaid over the model.

In such a way it is possible to visualize the anatomy of the relevant region of the patient body from the point of view of the tip of the medical device 1. Such visualization can further assist a physician in steering the medical device 1 during the interventional procedure. In this respect, the embodiments described above can also be combined such that it is possible to switch between a visualization in which the positions of the US sensors are marked 6 in the overlay of the live US images on the model and a visualization corresponding to the view as seen by the virtual eye.

In the system described above, particularly the US unit 3, the 3D model providing unit 5, the tracking unit 7 and the mapping unit 8 may be implemented as software modules executed on one or more computer device(s). For this purpose, a corresponding computer program is provided and installed on the computer device(s), which comprises instructions for executing the functions of the units. Further, the computer device(s) is/are particularly connected to the US probe 2 and the US sensor(s) 6 in order to control the operation of the US probe 2 and to receive US signals acquired by the US probe 2 and the US sensor(s) 6. Moreover, the computer device(s) is/are connected to the display unit 4 to control the display unit 4 to display the generated visualizations as explained above.

In the embodiments of the system described above, it is possible to generate visualizations of a model and live US images of a region of the patient body on the basis of the position and/or orientation of one medical device 1 included in the relevant region of the patient body, where the position(s) of US sensor(s) 6 attached to the medical device 1 are marked in the visualizations or where the visualizations correspond to the view as seen by a virtual eye at the location of a US sensor 6 attached to the tip of the medical device 1.

Figure 6:
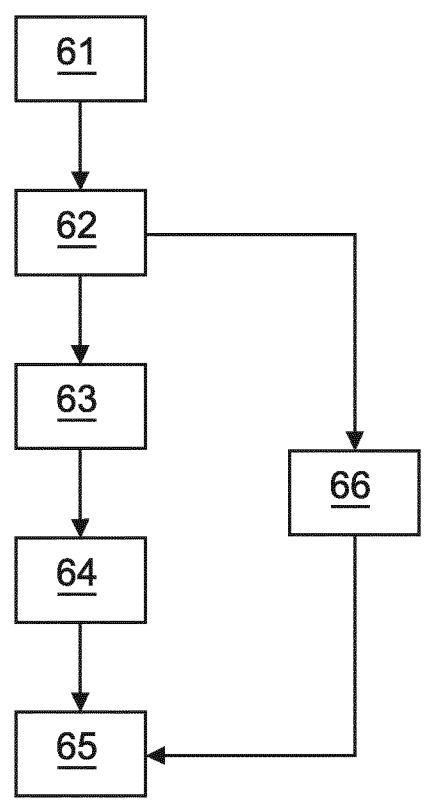

In FIG. 6, some of the steps of the related procedure are summarized. In the illustrated step 61, the three-dimensional model of the relevant region of the patient body is generated in the initialization phase as explained above. Thereupon, during the actual interventional procedure, live US images are acquired by means of the US probe 2 (step 62). Further, the relative position(s) of the US sensor(s) 6 attached to the medical device 1 and the US probe 2 is/are determined as explained above (step 63). These positions are mapped onto the model 21 by the mapping unit 8 (step 64). Moreover, the mapping unit 8 generates a visualization as described above in which the positions of the US sensor(s) are marked in the model 21 (step 65). In addition, the mapping unit may map the live US images acquired by means of the US probe onto the model 21 (step 66) and overlay the live US images over the model 21 accordingly in the generated visualization.

In a similar manner, it is also possible to generate corresponding visualizations with respect to a plurality of medical devices 1 used in the relevant region of the patient body.

In related embodiments, the positions of US sensors 6 attached to these medical devices 1 may all be marked in the visualizations and/or the mapping unit 8 may generate visualizations corresponding to views as seen by virtual eyes at the locations of the tips of the different medical devices 1. In the latter case, it may also be possible to switch between these visualizations. Moreover, the mapping unit 8 may mark in the visualization pertaining to one medical device 1 the positions of US sensor 6 attached to the other medical devices 1 if they are included in the field of view of the virtual eye at the tip of the relevant medical device 1. The corresponding marks may be positioned on the basis of a mapping of the positions of the US sensors 6 onto the field of view of the virtual eye.

Further, one embodiment of the system comprises that the medical device 1 is an EP catheter which is used for generating an electro-anatomical map of the relevant region of the patient body, such as a cardiac chamber. This map may be overlaid over the aforementioned visualizations generated in the system on the basis of the model and may include an activation map indicating local activation times and/or a voltage map indicating local electrogram amplitudes. The EP catheter may comprise a plurality of electrodes for sensing electrical signals and optionally for delivering stimulation signals and on the basis of the sensed electrical signals, local activation times and/or electrogram amplitudes are determined in a way known to a person skilled in the art. For generating the activation and/or voltage map, the EP catheter is moved within the relevant region of the patient body and local measurements are made at different locations within the region. At each measurement location, the positions of the electrodes are determined on the basis of the US signals sensed by means of the US sensor(s) 6 attached to the EP catheter as explained above. Then, the results of the local measurements are combined to generate the map and the mapping unit 8 may overlay the map onto the model of the relevant region of the patient body on the basis of the recorded position ad orientation information.

Moreover, the generated visualizations may be fused with fluoroscopy images of the relevant region of the patient body acquired using a fluoroscopy device.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system, comprising:
 an ultrasound probe configured to obtain a plurality of ultrasound images during live imaging, the plurality of ultrasound images showing a portion of a heart; and
 a computer configured for communication with the ultrasound probe, wherein the computer is configured to:
  generate a three-dimensional (3D) model of the heart that is distinct from the plurality of ultrasound images;
  determine at least one of a relative position or a relative orientation of an ultrasound sensor with respect to the ultrasound probe, wherein the ultrasound sensor is coupled to a cardiac medical device that is distinct from the ultrasound probe;
  determine, in the 3D model, the portion of the heart shown in the plurality of ultrasound images, based on the at least one of the relative position or the relative orientation, wherein the 3D model depicts:
   the portion of the heart shown in the plurality of ultrasound images; and other portions of the heart;
  generate a visualization; and
  provide the visualization to a display in communication with the computer,
 wherein, to generate the visualization, the computer is configured to overlay, during the live imaging, the plurality of ultrasound images on only the portion of the heart in the 3D model.

2. The system of claim 1, wherein the computer is configured to:
 map the plurality of ultrasound images onto the 3D model; and
 overlay the 3D model with the plurality of ultrasound images based on the mapping of the plurality of images onto the 3D model.

3. The system of claim 2,
 wherein the computer is configured to compare the plurality of ultrasound images from the live imaging and the 3D model,
 wherein the computer is configured to perform the mapping based on the comparison.

4. The system of claim 2,
 wherein the computer is configured to perform the mapping based on a position and orientation of the ultrasound probe with respect to a reference frame associated with the 3D model.

5. The system of claim 1,
 wherein the ultrasound probe is configured to obtain a different plurality of ultrasound images during an initialization phase different than the plurality of ultrasound images, and
 wherein the computer is configured to generate the 3D model using the different plurality of ultrasound images.

6. The system of claim 1,
 wherein the computer is configured to receive imaging data comprising a modality different than ultrasound,
 wherein the computer is configured to generate the 3D model using the imaging data.

7. The system of claim 1,
 wherein the heart undergoes a periodic motion having different motion phases, and
 wherein the 3D model is a dynamic model comprising a deforming sub-model for each of the different motion phases.

8. The system of claim 1,
 wherein the computer is configured to map a position and orientation of the ultrasound probe onto the 3D model, and
 generate the visualization based on the mapping of the position and orientation of the ultrasound probe onto the 3D model.

9. The system of claim 1, wherein the ultrasound sensor is configured to sense ultrasound signals emitted by the ultrasound probe.

10. The system of claim 9, wherein determining the relative position and the relative orientation of the ultrasound sensor with respect to the ultrasound probe is based on the sensed ultrasound signals; and
 wherein the computer is configured to map the relative position of the ultrasound sensor onto the 3D model.

11. The system of claim 10, wherein a position of the ultrasound sensor is marked in the visualization.

12. The system of claim 9,
 wherein the visualization comprises a view of the 3D model and the plurality of ultrasound images overlaid on the 3D model from a perspective of the ultrasound sensor.

13. The system of claim 9, wherein the computer is configured to generate the visualization based on:
mapping a position and orientation of the ultrasound probe onto the 3D model; and
the relative position and the relative orientation of the ultrasound sensor with respect to the ultrasound probe.

14. The system of claim 9,
wherein the ultrasound probe is configured to emit ultrasound signals into different directions,
wherein the computer is configured to determine the relative position of the ultrasound sensor based on at least one of:
a reception level of the ultrasound signals in the ultrasound sensor; or
a time difference between emission of the ultrasound signals by the ultrasound probe and sensing of the ultrasound signals by the ultrasound sensor.

15. The system of claim 9,
wherein the cardiac medical device is configured to carry out electrical measurements,
wherein the computer is configured to:
generate an electro-anatomical map based on the electrical measurements; and
overlay the electro-anatomical map on the 3D model based on the relative position of the ultrasound sensor with respect to the ultrasound probe during the electrical measurements.

* * * * *